United States Patent [19]

Shionoya et al.

[11] 4,414,201

[45] Nov. 8, 1983

[54] IMMUNOPOTENTIATOR CONTAINING ABRIN

[75] Inventors: Hiroshi Shionoya, Tokorozawa; Haruyoshi Arai, Inuyama; Nozomu Koyanagi, Niiza; Hitoshi Takeuchi, Tokyo, all of Japan

[73] Assignee: Eisai Co., Ltd., Tokyo, Japan

[21] Appl. No.: 384,324

[22] Filed: Jun. 1, 1982

Related U.S. Application Data

[63] Continuation of Ser. No. 204,786, Nov. 7, 1980, abandoned.

[30] Foreign Application Priority Data

Nov. 9, 1979 [JP] Japan ................. 54-144326

[51] Int. Cl.³ .............. A61K 37/00; A61K 39/00
[52] U.S. Cl. ........................ 424/88; 424/177
[58] Field of Search ................. 424/88, 177

[56] References Cited

FOREIGN PATENT DOCUMENTS 1522600  8/1978  United Kingdom .

OTHER PUBLICATIONS

Olsnes et al., The Journal of Immunology, vol. 113, No. 3, Sep. 1974, pp. 842–847.
Biochem. & Biophysical Research Communicators, vol. 88, No. 3, 1979, Jun. 13, 1979, pp. 818–825.
Davis et al., Microbiology, Harper & Row Publishers (1967), pp. 458–459.
Jung–Low Lin et al., J. Formosan Med. Assoc. 68, No. 6, pp. 322–324 (1969).
Proteins, Nucleic Acids, Enzymes; separate print Immuno–Biochemistry, vol. 11, No. 15, pp. 1506–1508 (1966).
Robinson et al., Scand. J. Immunol., 5, 299–304 (1976).
Olsnes et al., J. Biol. Chem. 249, 803–810 (1974).
The Merck Index, 9th Edition (1976), p. 1.
Olsnes et al., Nature, vol. 249 (1974), pp. 627–630.

Primary Examiner—Stanley J. Friedman
Attorney, Agent, or Firm—Wenderoth, Lind & Ponack

[57] ABSTRACT

An immunopotentiator comprising abrin as an active ingredient. Abrin is a glucoprotein having a molecular weight of about 65,000 and can be used in the form of an aqueous solution. It is useful for prevention and treatment of bacterial and viral infections.

1 Claim, No Drawings

IMMUNOPOTENTIATOR CONTAINING ABRIN

This application is a continuation of application Ser. No. 204,786, filed Nov. 7, 1980, now abandoned.

BACKGROUND OF THE INVENTION

This invention relates to an immunopotentiator comprising abrin as an active ingredient.

Abrin used in this invention is a lectin isolated from the seeds of jequirity (Abrus precatorius) which is a plant of the family Leguminosae occurring naturally in the tropical and subtropical zones. It is a kind of glycoprotein having a molecular weight of about 65,000.

Immune protection in vertebrates is known to be provided by two basic immune response systems against infections and tumor cells. One is the cellular immune response system effective mainly against infections by fungi, viruses, intracellular parasitic bacteria, etc. and against tumor cells, and the other is the humoral immune response system effective for defence mainly against infections by viruses and extra-cellular parasitic bacteria.

A substance which when injected into a living organism together with an antigen, increases the aforesaid immune responses to the antigen is known as an immuno-adjuvant [Davis, B. D. et al., Microbiology, Harper & Row Publishers, page 458, (1967)]. Heretofore, the Freund's complete adjuvant has been used mainly as the immuno-adjuvant. Since, however, the Freund's complete adjuvant is composed of killed Mycobacteria, a surface-active agent and a mineral oil, a complex operation is required for formulating it into a dosage form by mixing it with an antigen in the form of an aqueous solution, a suspension, etc., and moreover, strong necrosis or swelling occurs at the injected site. Accordingly, the Freund's complete adjuvant has been unable to be used in humans.

SUMMARY OF THE INVENTION

It is an object of this invention to provide an immunopotentiator having the ability to increase both cellular and humoral immune responses.

According to this invention, there is provided an immunopotentiator comprising abrin as an active ingredient.

DETAILED DESCRIPTION OF THE INVENTION

Abrin used as the active ingredient of the immunopotentiator of this invention is an immuno-adjuvant having the ability to potentiate both the aforesaid cellular and humoral immune responses. It is characterized by having a strong adjuvant activity in amounts which do not cause necrosis, swelling, etc. at a site of injection. The abrin in accordance with this invention also has the advantage that since it can be used in the form of an aqueous solution, it can be easily formulated into a dosage form by mixing with an antigen.

Jung-Yaw Lin et al., J. Formosan Med. Assoc. 68, No. 6, 322-324 (1969) reported that the acute toxicity ($LD_{50}$) of abrin used in this invention is 0.020 mg/kg (mouse, i.p.). Experiments of the present inventors showed that $LD_{50}$ of abrin is 12 μg/kg (mouse, i.p.).

When administered to man and animals, the abrin of this invention increases immune responses to bacteria, viruses and other microorganisms and tumor cells, and is therefore useful for prevention and treatment of infections by microorganisms such as bacteria and viruses or cancer.

The minimum dosage of abrin which shows an immunopotentiating activity is about 3 ng per human or animal irrespective of body weight. The maximum dosage is generally about 1 to about 1.5 μg/kg. These dosages are much lower than the lethal dose mentioned above.

Abrin in accordance with this invention may be administered together with various antigens, and the preferred route of administration is subcutaneous, intramuscular or intraperitoneal. Furthermore, abrin can be administered separately from an antigen, and in this case, intravenous and intrapleural administrations are possible in addition to the aforesaid administration routes. Or it may be administered directly to a tumor region. The administrations of abrin are preferably twice a week to once in two weeks.

In administration, the abrin in accordance with this invention may be formulated into any desired injectable form by known formulating methods. For example, it may be in the form of an injecting ampoule containing 0.1 to 1 ml of a physiological saline or a neutral to weakly acidic buffer containing abrin in a concentration of about 100 μg to 1 mg/ml, or an abrin-containing lyophilized ampoule.

The immunopotentiating activity of abrin is illustrated specifically by the following Examples.

EXAMPLE 1

Immunopotentiative Effect of Abrin on Production of Humoral Antibody in Mice

The effect of abrin on the production of a humoral antibody in mice (female CDF 1) each having a body weight of 20 to 23 g was examined using bovine serum albumin (BSA) as an antigen.

A group of 5 mice (Group 1) was primarily immunized by injecting subcutaneously at their backs 0.2 ml of physiological saline containing 15 ng of abrin and 1 μg of BSA. Two weeks after the primary immunization, secondary immunization was performed by injecting subcutaneously into their backs 0.2 ml of a physiological saline containing 15 ng of abrin and 1 μg of BSA.

Another five mice (Group 2) were each primarily immunized by simultaneously injecting subcutaneously 0.1 ml of a physiological saline containing 1 μg of BSA at the right side of their backs, and 0.1 ml of a physiological saline containing 15 ng of abrin into the left side of their backs. Two weeks later, the mice were secondarily immunized by injecting subcutaneously into the same sites as above 0.1 ml of a physiological saline containing 15 ng of abrin and 0.1 ml of a physiological saline containing 1 μg of BSA separately.

Other five mice (Control Group) were treated with 0.2 ml of a physiological saline containing 1 μg of BSA in the same way as in the case of the Group 1.

Blood was taken from the mice in each of the groups seven days after the secondary immunization, and the plasma was separated. The antibody titer of the plasma was measured in accordance with a method of hemagglutination of tanned red blood cells of sheep passively sensitized with BSA [PROTEINS, NUCLEIC ACIDS, ENZYMES; separate print "IMMUNO-BIOCHEMISTRY", Vol. 11, No. 15, page 1506, (1966)]. The results are shown in Table 1.

TABLE 1

Ability of abrin to increase production of an anti-BSA antibody

| Group | Immunization | Antibody titer (HA titer*) (Dilution of the plasma ± S.E.**) | Significance of difference from the control |
|---|---|---|---|
| Control | BSA (1 μg) | $10 \times 2^{1.0 \pm 0.6}$ | |
| 1 | A mixture of abrin (15 ng) and BSA (1 μg) was administered by injection. | $10 \times 2^{5.80 \pm 0.7}$ | $p < 0.01$ |
| 2 | Abrin (15 ng) and BSA (1 μg) were separately administered by injection. | $10 \times 2^{4.6 \pm 1.5}$ | $p < 0.05$ |

*HA titer: hemagglutination titer
**S.E.: Standard error

It is seen from Table 1 that abrin provides an increased immune response to an antigen, and that this effect is stronger when abrin is administered together with the antigen (Group 1), as compared with the effects of the separate administration of abrin and the antigen. Furthermore, it is noted that abrin shows appreciable adjuvant activity even when administered separately from the antigen (Group 2).

EXAMPLE 2

Immunopotentiative Effect of Abrin on Production of a Humoral Antibody in Mice

A solution (0.2 ml) obtained by mixing 0.1 ml of a physiological saline containing 1 μg of BSA antigen with 0.1 ml of a physiological saline containing abrin in various amounts from 0.1 ng to 30 ng was subcutaneously injected into mice (female CDF 1) having a body weight of 20 to 23 g. Two weeks later, the same solution was injected into the mice in the same manner. Twelve days after the second injection, blood was taken from each of the mice, and the plasma was separated. The antibody titer of the plasma was measured in the same way as described in Example 1, and the results are shown in Table 2.

TABLE 2

Activity of abrin to increase production of an anti-BSA antibody

| Dose of abrin (ng/mouse) | Number of animals | Number of mice having plasma HA titer estimated by BSA-sensitized sheep red blood cell hemagglutination reaction HA titer | | | | |
|---|---|---|---|---|---|---|
| | | 0 | 20 | 40 | 80 | 160 |
| 0 | 10 | 10 | | | | |
| 0.1 | 5 | 5 | | | | |
| 0.3 | 5 | 4 | | 1 | | |
| 1.0 | 5 | 3 | 1 | | 1 | |
| 3.0 | 4 | 1 | | 3 | | |
| 10.0 | 5 | | | | 1 | 4 |
| 30.0 | 5 | 1 | 1 | 2 | | 1 |

It is seen from Table 2 that the activity of abrin to increase the humoral immunity is noted in 1 ng to 30 ng per mouse, and is the strongest at a dose of 10 ng.

EXAMPLE 3

Immunopotentiative Effect of Abrin on Cellular Immune Response in Mice

A physiological saline (0.2 ml) containing 1 μg of BSA and various amount of abrin was injected subcutaneously into the back of each of mice (female CDF 1) having a body weight of 20 to 23 g, and two weks later, the mice were treated with injection in the same way as above (secondary immunization). Thirty-nine days after the secondary immunization, 10 μl of a physiological saline containing 10 μg of BSA was injected subcutaneously into the auricle of each mouse (challenge), in accordance with the method of J. H. Robinsons et al. [Scand. J. Immunol., 5, 299 (1976)]. Twenty-four hours later, an ear swelling was measured. The results are shown in Table 3.

TABLE 3

Activity of abrin to increase cellular immune response

| Group | Number of animals | Immunization Abrin (ng/mouse) | Immunization BSA (μg/mouse) | Challenge BSA (μg/mouse) | Ear swelling ($10^{-3}$ cm ± S.E.**) | Significance of the difference from the control (P) |
|---|---|---|---|---|---|---|
| Control | 6 | 0 | 1 | 10 | 5.0 ± 0.2 | |
| 1 | 5 | 1 | 1 | 10 | 3.6 ± 1.4 | ns* |
| 2 | 5 | 10 | 1 | 10 | 12.0 ± 1.7 | <0.01 |
| 3 | 4 | 30 | 1 | 10 | 14.0 ± 2.3 | <0.01 |

*ns: not significant;
**S.E.: standard error

The results given in Table 3 demonstrate that at a dose of 10 ng and 30 ng, abrin increases the cellular immune response to BSA.

EXAMPLE 4

Immunopotentiative Effect of Abrin on Humoral Immune Response in Rabbits

A physiological saline (0.5 ml) containing 1 μg of BSA and 10 ng or 100 ng of abrin was injected subcutaneously into native Japanese white male rabbits having a body weight of 2.5 to 3 kg at both sides of their back in a dose of 0.25 ml at each side. The date of the first injection was designated as 0 day, and the rabbits were immunized by injecting the same physiological saline in the same way as in the first injection on the 14th, 22nd and 55th days. Blood was taken from the ear vein of each rabbit immediately before each injection and on the 29th and 68th days (six times in total), and the serum was separated. An aliquot (0.2 ml) of the serum was mixed with 0.2 ml of 0.2M 2-mercaptoethanol dissolved in the Dulbecco's phosphate buffer (pH 7.2) [to be abbreviated as PBS (pH 7.2)]. The mixture was allowed to stand for 17 hours at 4° C., and in a dialyzing cellophane tube, was dialyzed at 4° C. for 15 hours against a 0.02M monoiodoacetamide in PBS (pH 7.2), and then against PBS (pH 7.2). On the next day, the serum within the cellophane tube was taken out to obtain a 2-mercaptoethanol-treated serum.

The anti-BSA antibody titer of the serum of each rabbit before and after treatment with 2-mercaptoethanol was measured by the hemagglutination of tanned sheep red blood cells passively sensitized with BSA. The results are shown in Table 4.

TABLE 4

Immunopotentiative effect of abrin on production of an anti-BSA antibody in rabbits

| Rabbit No. | Dose of abrin (ng/rabbit) | Anti-BSA antibody titer (HA titer) Before treatment with 2ME(*)/after treatment wtih 2ME | | | | |
|---|---|---|---|---|---|---|
| | | 14th day | 22nd day | 29th day | 55th day | 68th day |
| 1 | 100 | 128/0 | 4/0 | 16/0 | 4/4 | 8/8 |
| 2 | 100 | 512/0 | 256/0 | 64/0 | 16/16 | 32/32 |
| 3 | 100 | 128/0 | 4/0 | 16/8 | 8/8 | 128/64 |
| 4 | 10 | 512/0 | 32/0 | 16/4 | 8/8 | 128/128 |
| 5 | 10 | 256/0 | 0/0 | 0/0 | 0/0 | 64/0 |
| 6 | 10 | 32/0 | 0/0 | 4/0 | 0/0 | 32/4 |
| Control | | | | | | |
| 7 | 0 | 64/0 | 0/0 | 0/0 | 0/0 | 0/0 |
| 8 | 0 | 0/0 | 0/0 | 0/0 | 0/0 | 0/0 |
| 9 | 0 | 0/0 | 0/0 | 0/0 | 0/0 | 0/0 |
| 10 | 0 | 0/0 | 0/0 | 0/0 | 0/0 | 0/0 |

(*)2ME: 2-mercaptoethanol

It is known that there exist two types of antibody having different physicochemical properties, i.e., IgM and IgG. While IgM is produced only transiently, IgG is produced continuously. Treatment of the antiserum with 2-mercaptoethanol selectively inactivates only the IgM antibody, and does not affect the activity of the IgG antibody. Accordingly, in the above Table 4, the anti-BSA antibody titer before treatment with 2-mercaptoethanol shows the total activity of the IgM antibody and the IgG antibody, and the anti-BSA antibody titer after the treatment shows the activity of the IgG antibody.

The results given in Table 4 demonstrate that at a dose of 10 ng and 100 ng, abrin exhibits immunopotentiating activity, and promotes shift from potentiation of IgM antibody production which is transient to potentiation of IgG antibody production which is continuous.

EXAMPLE 5

Potentiation of Immunogenicity of Inactivated Tumor Cell Vaccine Due to the Addition of Abrin Balb/c mice were inplanted into peritoneally with $1 \times 10^7$ syngenic Meth-A ascitic tumor cells. The tumor cells were obtained from pelitoneal cavity of the tumor bearing mice 1 week after the inplantation and washed with Eagle's minimum essential medium (hereafter referred to MEM).

Five ml of the tumor cell suspension ($1 \times 10^8$/ml in MEM) were placed into a plastic dish of 4 cm in diameter. The suspension was then irradiated 9000 R from a cobalt source to prepare an inactivated Meth-A tumor cell vaccine. The vaccine was diluted with MEM to the concentration of $2 \times 10^7$/ml. To the diluted cell suspension was added the equal volume of MEM which contains abrin in the concentration 120 ng/ml. One tenth of the resulting tumor cell suspension added abrin was injected subcutaneously to Balb/c mice on their right side of the back to effect the immunization. The mice were challenged subcutaneously with $1 \times 10^6$ viable Meth-A tumor cells on the left side of the back 2 weeks after the immunization.

Activity of vaccine was measured by rejection ratio (percentage) of transplanted tumor cells. The results are shown in the following Table 5.

TABLE 5

Potentiation by abrin of inactivated Meth-A tumor cell vaccine

| Group | Immunization | Number of tumor-free mice Number of challenged mice (Percentage) | Significant difference* |
|---|---|---|---|
| 1 | $1 \times 10^6$ irradiated cells plus abrin | 20/20 (100%) | |
| 2 | $1 \times 10^6$ irradiated cells alone | 16/25 (64%) | <0.003 |
| 3 | Non-immune | 0/12 (0%) | <0.00001 |

*Probability test as compared with Group 1 by Fisher's exact test.

The Table 5 discloses that the rejection ratio in Group 2 that was immunized with irradiated tumor cells alone amounts to 16/25 (64%). On the contrary, the rejection ratio in Group 1 that was immunized with irradiated tumor cells plus abrin (6 ng) amounts to 20/20 (100%). It was thus proved that the addition of abrin significantly potentiated the immune response to an inactivated tumor cell vaccine, i.e. abrin was an adjuvant that enhances antitumor immunity.

EXAMPLE 6

Preparation of an Abrin-Containing Ampoule

Glacial acetic acid (0.05 ml) was added on ice water bath to 5 ml of an aqueous suspension containing abrin crystals in a concentration of 10 mg/ml to dissolve the abrin crystals. To the resulting solution was added 10 ml of a 0.01M phosphate buffer (pH 6.0) containing 0.15M of sodium chloride [to be abbreviated as PBS (pH 6.0)]. Then, 0.4 ml of a 1M $Na_2HPO_4$ solution was added to adjust the pH of the solution to about 5. The solution was centrifuged at 15,000 rpm for 10 minutes. The supernatant solution was filtered by a 0.45 μm filter (Millipore Filter, type HA) to remove microbes. The filtrate was put into a cellophane tube, and dialyzed overnight against 5 liter of PBS (pH 6.0).

The dialyzate was diluted with PBS (pH 6.0) to form a solution containing abrin in a concentration of 500 μg/ml. The concentration of abrin was adjusted according to its $E_{280\ nm}^{1\%}$ value of 15.9 reported by Olsnes et al. [J. Biol. Chem. 249, 803–810 (1974)]. The abrin solution was put separately in an amount of 0.1 ml into each of 1 ml glass ampoules to prepared injecting ampoules each containing 50 μg of abrin.

What is claimed is:

1. A method for enhancing immune response to intracellular and extra-cellular parasitic bacteria in a human or animal subject in need of such treatment which comprises parenterally administering abrin to such human or animal subject in an amount of from at least about 3 ng per human or animal subject up to 1.5 μg/kg of the body weight of the human or animal subject.

* * * * *